United States Patent [19]
Henkelmann et al.

[11] Patent Number: 5,783,706
[45] Date of Patent: Jul. 21, 1998

[54] PROCESS FOR THE PREPARATION OF 1,3-DISUBSTITUTED IMIDAZOLIDINONES

[75] Inventors: Jochem Henkelmann, Mannheim; Thomas Rühl, Frankenthal, both of Germany

[73] Assignee: BASF Aktiengesellschaft, Ludwigshafen, Germany

[21] Appl. No.: 776,105

[22] PCT Filed: Jul. 18, 1995

[86] PCT No.: PCT/EP95/02806

§ 371 Date: Mar. 17, 1997

§ 102(e) Date: Mar. 17, 1997

[87] PCT Pub. No.: WO96/02516

PCT Pub. Date: Feb. 1, 1996

[30] Foreign Application Priority Data

Jul. 20, 1994 [DE] Germany .......................... 44 25 696.5

[51] Int. Cl.⁶ .................... C07D 233/32; C07D 233/58
[52] U.S. Cl. .................... 548/316.4; 548/325.5; 548/326.1
[58] Field of Search .................... 548/326.1, 316.4, 548/325.5

[56] References Cited

U.S. PATENT DOCUMENTS

| | | | |
|---|---|---|---|
| 2,422,400 | 6/1947 | Farlow | 260/309 |
| 2,892,843 | 6/1959 | Levine | 548/316.4 |
| 4,617,400 | 10/1986 | Ito et al. | 548/317 |

FOREIGN PATENT DOCUMENTS

| | | |
|---|---|---|
| 183 076 | 6/1986 | European Pat. Off. . |
| 198 345 | 10/1986 | European Pat. Off. . |
| 1545614 | 8/1965 | Germany . |
| 59155364 | 2/1983 | Japan . |
| 1173432 | 12/1960 | United Kingdom . |
| 1517820 | 7/1978 | United Kingdom . |

OTHER PUBLICATIONS

Bogatsky et al., *Synthesis*, 1982, pp. 464–465.
Li et al., *J. Med. Chem.*, vol. 24, 1981, pp. 1089–1092.
Mikheev et al., *J. Org. Chem. USSR*, 1983, pp. 436–439.
Dyer et al., *J. Amer. Chem. Soc.*, vol. 79, 1957, pp. 672–675.

*Primary Examiner*—Floyd D. Higel
*Attorney, Agent, or Firm*—Keil & Weinkauf

[57] ABSTRACT

2-Imidazolidinones are prepared by reacting 1,3-dioxalan-2-one (ethylene carbonate) with at least one compound of the formula $RNH_2$ where R can be, inter alia, H, alkyl, aryl, heteroalkyl or heteroaryl.

9 Claims, No Drawings

PROCESS FOR THE PREPARATION OF 1,3-DISUBSTITUTED IMIDAZOLIDINONES

This application is a 371 of PCT/EP95/02806, filed Jul. 20, 1994.

The present invention relates to the preparation of 1,3-disubstituted 2-imidazolidinones from 1,3-dioxalan-2-one (ethylene carbonate) and primary amines.

1,3-Disubstituted 2-imidazolidinones, in particular 1,3-dimethyl-2-imidazolidinone, are interesting polar, aprotic solvents in particular for high molecular weight compounds such as polyamides, polyvinyl chloride, polyvinyl alcohol, polystyrene, polyurethane and phenol resins. Furthermore, 1,3-disubstituted 2-imidazolidinones are used in the textile industry as finishing agents.

Synthesis of 1,3-disubstituted imidazolidinones has been described many times. Catalytic hydrogenation of 1,3-dimethoxymethyl- or 1,3-dihydroxymethyl-2-imidazolidinone formed as intermediate and of other N,N'-dihydroxymethyl-substituted cyclicureas (U.S. Pat. No. 2,422,400; U.S. Pat. No. 4,617,400) takes place with extensive residue formation. Alkylation of cyclic ureas (Synthesis (1982), 464; J. Med. Chem. 24, 1089, (1981)) requires besides the stoichiometric amount of a base toxicologically objectionable alkyl halides. Reactions of N,N'-disubstituted diamines with urea (EP 198 345), which must be carried out in a solvent, or with the toxicologically objectionable phosgene (EP 183 076) are likewise known. Also described are syntheses from carbon dioxide, primary amine and ethylene glycol (JP 5 9155-364-A) or dichloroethane, and the Leukart-Wallach reaction for synthesizing 1,3-dimethylimidazolidinone, which requires a heterogeneous hydrogenation catalyst (GB 1517820; DE 1545614; U.S. Pat. No. 2,422,400).

It is an object of the present invention to develop a synthetic route for 1,3-disubstituted 2-imidazolidinones which is simple and economic. It is intended in particular that the process be superior to known synthetic routes from the environmental viewpoint.

We have found that this object is achieved by a process as defined in the claims. Preferred embodiments are indicated in the dependent claims and in the following description.

It has been found, surprisingly, that ethylene carbonate can be reacted with primary amines to give the required cyclic urea directly without solvent or catalysts being necessary.

The invention therefore relates to a process for preparing 2-imidazolinones of the general formula (I)

$$\underset{\underset{\diagdown N\diagup}{R\diagdown N\diagup\overset{O}{\overset{\|}{C}}\diagdown N\diagup R}}{}$$ (I)

in which the radicals R, which can be identical or different, are a) straight-chain, branched or cyclic alkyl radicals with 1 to 12 carbon atoms, which can in turn be substituted by $C_{6-10}$-aryl, F, Cl, Br;

b) aryl radicals with 6 to 10 carbon atoms, which can in turn be substituted by $C_{1-12}$-alkyl;

c) heteroalkyl radicals in which the alkyl radicals as defined above are interrupted by one or more heteroatoms selected from O, S and N, d) heteroaryl radicals with 5 to 10 ring atoms which contain 1 to 3 heteroatoms selected from O, S, N, which comprises reacting 1,3-dioxalan-2-one (ethylene carbonate) with at least one compound of the general formula (II)

$$RNH_2 \qquad \qquad (II)$$

where R has the above meaning. A preferred product of the process is 1,3-dimethyl-2-imidazolidinone.

The reaction is generally carried out at from 150° C. to 300° C., preferably 200° C. to 250° C., particularly preferably under autogenous pressure. The autogenous pressure which is set up is usually from 50 to 150 bar, depending on the amine.

The amount of primary amine employed relative to ethylene carbonate is advantageously stoichiometric or more than stoichiometric, eg. 5×stoichiometric, preferably in the region of a 1.5 to 3×stoichiometric excess.

A reaction time of up to about 24 hours has frequently proven sufficient.

The yield of the process can generally be increased by using water. The amount of water employed can be up to 50% by weight, advantageously 30 to 45% by weight, based on ethylene carbonate employed.

The reaction mixture can be worked up by simple distillation of the crude product.

EXAMPLE 1

500 g of ethylene carbonate, 500 g of methylamine and 200 g of water were introduced at room temperature into an autoclave and heated at 250° C. for 24 hours. The autogenous pressure of the reaction reached 120 bar.

The mixture was subsequently cooled, decompressed and distilled. 550 g of 1,3-dimethyl-2-imidazolidinone (R=CH$_3$ in formula (I)) (85% of theory) were obtained at 60° C. under 2 mbar.

EXAMPLE 2

The same mixture as in Example 1 but without water was heated at 250° C. for 24 hours. Subsequent workup afforded 476 g of 1,3-dimethyl-2-imidazolidinone (75% yield).

EXAMPLE 3

500 g of ethylene carbonate were reacted with 350 g of methylamine and worked up as in Example 1. The yield of 1,3-dimethyl-2-imidazolidinone was 55%.

EXAMPLE 4

Ethylene carbonate and methylamine were reacted as in Example 3, but at 200° C., and worked up. The yield was 42%.

EXAMPLE 5

Ethylene carbonate and methylamine were reacted as in Example 3, but at 300° C., and worked up. The yield was 45%.

We claim:

1. A process for the preparation of a 2-imidazolidinone of the formula (I)

$$\underset{\underset{\diagdown N\diagup}{R\diagdown N\diagup\overset{O}{\overset{\|}{C}}\diagdown N\diagup R}}{}$$ (I)

wherein the radicals R, which are identical or different, are a) straight-chain, branched or cyclic alkyl radicals with 1 to 12 carbon atoms, which are unsubstituted or substituted by $C_{6-10}$-aryl, F, Cl, Br;

b) aryl radicals with 6 to 10 carbon atoms, which are unsubstituted or substituted by $C_{1-12}$-alkyl;

c) heteroalkyl radicals in which the alkyl radicals as defined above are interrupted by one or more heteroatoms selected from O, S and N;

d) heteroaryl radicals with 5 to 10 ring atoms which contain 1 to 3 heteroatoms selected from O, S and N, which comprises reacting 1,3-dioxolan-2-one (ethylene carbonate) with a least one compound of the formula (II)

$$R-NH_2 \qquad (II)$$

where R has the above meaning.

2. The process of claim 1, wherein the reaction is carried out with a stoichiometric or more than stoichiometric amount of an amine (II) relative to 1,3-dioxolan-2-one.

3. The process of claim 1, wherein the reaction is carried out at from 150° to 300° C.

4. The process of claim 1, wherein the reaction is carried out in the presence of water in an amount of up to 50% by weight based on 1,3-dioxolan-2-one.

5. The process of claim 1, wherein methyl amine is used as the primary amine of the formula (II).

6. The process of claim 1, wherein the 2-imidazolidinone is isolated by distillation.

7. The process of claim 1, wherein the reaction is carried out with a 1.5 to 3×stoichiometric excess of an amine (II) relative to 1,3-dioxolan-2-one.

8. The process of claim 1, wherein the reaction is carried out at from 200° to 250° C.

9. The process of claim 1, wherein the reaction is carried out in the presence of water in an amount of from 30 to 45% by weight based on 1,3-dioxolan-2-one.

* * * * *